United States Patent
Xie et al.

(10) Patent No.: US 9,114,126 B2
(45) Date of Patent: Aug. 25, 2015

(54) NA/K-ATPASE LIGANDS, OUABAIN ANTAGONISTS, ASSAYS AND USES THEREOF

(71) Applicant: The University of Toledo, Toledo, OH (US)

(72) Inventors: Zi-Jian Xie, Saline, MI (US); Joseph I. Shapiro, Toledo, OH (US); Shuyi Si, Beijing (CN); Zhongbing Zhang, Beijing (CN)

(73) Assignee: THE UNIVERSITY OF TOLEDO, Toledo, OH (US)

( * ) Notice: Subject to any disclaimer, the term of this patent is extended or adjusted under 35 U.S.C. 154(b) by 0 days.

(21) Appl. No.: 14/045,269

(22) Filed: Oct. 3, 2013

(65) Prior Publication Data

US 2014/0031419 A1  Jan. 30, 2014

Related U.S. Application Data

(62) Division of application No. 13/395,700, filed as application No. PCT/US2010/048227 on Sep. 9, 2010.

(60) Provisional application No. 61/243,036, filed on Sep. 16, 2009.

(51) Int. Cl.
  *A61K 31/353* (2006.01)
  *A61K 31/35* (2006.01)
  *A61K 31/352* (2006.01)

(52) U.S. Cl.
  CPC ............... *A61K 31/353* (2013.01); *A61K 31/35* (2013.01); *A61K 31/352* (2013.01)

(58) Field of Classification Search
  None
  See application file for complete search history.

(56) References Cited

U.S. PATENT DOCUMENTS

| | | |
|---|---|---|
| 2,698,822 A | 1/1955 | Halpern et al. |
| 3,122,475 A | 2/1964 | Schaeppi |
| 3,687,944 A | 8/1972 | Pettit et al. |
| 4,261,971 A | 4/1981 | Appelgren et al. |
| 5,153,178 A | 10/1992 | Maroko |
| 5,888,527 A | 3/1999 | Nashimoto et al. |
| 5,965,540 A | 10/1999 | Waller |

(Continued)

FOREIGN PATENT DOCUMENTS

| | | |
|---|---|---|
| CN | 101374571 A | 2/2009 |
| CN | 101541319 A | 9/2009 |

(Continued)

OTHER PUBLICATIONS

Dorwald F. Zaragoza. Side reviews in organic chemistry: a guide to successful synthesis design. Weinheim: WILEY-VCH, Verlag, GMBH & Co., KGaA, 2005. Preface.*

(Continued)

*Primary Examiner* — Anna Pagonakis
(74) *Attorney, Agent, or Firm* — MacMillan, Sobanski & Todd, LLC

(57) ABSTRACT

The present disclosure relates to methods of inhibiting the ATPase activity of Na/K-ATPase without stimulating the receptor function, methods of blocking Na/K-ATPase interaction with Src, methods of inhibiting cell growth, and methods of abolishing ouabain-provoked signaling transduction in the heart of a subject, which includes providing an effective amount of at least one hydroxyl xanthone derivative.

4 Claims, 13 Drawing Sheets
(9 of 13 Drawing Sheet(s) Filed in Color)

(56) References Cited

U.S. PATENT DOCUMENTS

| | | | |
|---|---|---|---|
| 6,071,885 | A | 6/2000 | Florkiewicz |
| 6,113,965 | A | 9/2000 | Goodsall et al. |
| 6,261,760 | B1 | 7/2001 | Fielding et al. |
| 6,562,864 | B1 | 5/2003 | Larson |
| 6,726,935 | B2 | 4/2004 | Ji et al. |
| 7,078,060 | B2 | 7/2006 | Burrell et al. |
| 7,157,493 | B2 | 1/2007 | Zhao et al. |
| 7,195,783 | B2 | 3/2007 | Shan et al. |
| 7,402,325 | B2 | 7/2008 | Addington |
| 7,858,126 | B2 | 12/2010 | Singh et al. |
| 8,283,441 | B2 | 10/2012 | Xie et al. |
| 8,394,434 | B2 | 3/2013 | Addington et al. |
| 8,524,286 | B2 | 9/2013 | Smothers |
| 2002/0039764 | A1 | 4/2002 | Rosen et al. |
| 2002/0055644 | A1 | 5/2002 | Winter et al. |
| 2002/0091085 | A1 | 7/2002 | Kay et al. |
| 2002/0168425 | A1 | 11/2002 | Nakayama et al. |
| 2004/0229275 | A1 | 11/2004 | Hayden et al. |
| 2005/0026849 | A1 | 2/2005 | Singh et al. |
| 2005/0271606 | A1 | 12/2005 | Iwasaki et al. |
| 2006/0004002 | A1 | 1/2006 | Thrash |
| 2006/0035835 | A1 | 2/2006 | Taniyama et al. |
| 2006/0094772 | A1 | 5/2006 | Chang et al. |
| 2006/0205679 | A1 | 9/2006 | Streeper et al. |
| 2007/0092970 | A1 | 4/2007 | Liang |
| 2007/0092972 | A1 | 4/2007 | Xiao et al. |
| 2007/0098765 | A1 | 5/2007 | Zhao et al. |
| 2007/0161589 | A1 | 7/2007 | Bennett et al. |
| 2008/0317878 | A1 | 12/2008 | Li et al. |
| 2009/0082293 | A1 | 3/2009 | Giordano et al. |
| 2009/0143279 | A1 | 6/2009 | Mootha et al. |
| 2009/0226513 | A1 | 9/2009 | Xie et al. |
| 2010/0056446 | A1 | 3/2010 | Xie et al. |
| 2010/0092585 | A1 | 4/2010 | Smothers |
| 2011/0245167 | A1 | 10/2011 | Xie et al. |
| 2012/0302630 | A1 | 11/2012 | Xie et al. |
| 2013/0011335 | A1 | 1/2013 | Xie et al. |

FOREIGN PATENT DOCUMENTS

| | | |
|---|---|---|
| WO | 97/34482 A1 | 9/1997 |
| WO | 02/14343 A1 | 2/2002 |
| WO | 02/092573 A2 | 11/2002 |
| WO | 03/016475 A2 | 2/2003 |
| WO | 2004/004785 A1 | 1/2004 |
| WO | 2004/043384 A2 | 5/2004 |
| WO | 2007/023011 A2 | 3/2007 |
| WO | 2007/089688 A2 | 8/2007 |
| WO | 2008/054792 A2 | 5/2008 |
| WO | 2010/053771 A1 | 5/2010 |
| WO | 2010/071767 A2 | 6/2010 |
| WO | 2011/034772 A1 | 3/2011 |
| WO | 2011/088208 A1 | 7/2011 |
| WO | 2011/088210 A1 | 7/2011 |

OTHER PUBLICATIONS

Canadian Notice of Requisition by the Examiner, Application No. 2,667,251, dated Dec. 13, 2013.
Chinese 1st Office Action, Application No. 201180010298.9, dated Aug. 16, 2013.
Chinese 2nd Office Action, Application No. 200980149736.2, dated Oct. 15, 2013.
Chinese 3rd Office Action, Application No. 200780043725.7, dated Jun. 12, 2012.
Chinese 4th Office Action, Application No. 200780043725.7, dated Nov. 15, 2012.
Chinese First Office Action, Application No. 200780003862.8, dated Jun. 30, 2011.
Chinese First Office Action, Application No. 201180010295.5, dated May 22, 2013.
Chinese Notification of the First Office Action, Appln. No. 201080046743.2, dated Apr. 25, 2013.
Chinese Office Action, Application No. 200980149736.2 dated Nov. 28, 2012.
Chinese Office Action, Application No. 200780043725.7 dated Jan. 12, 2011.
Chinese Second Office Action, Application No. 201180010295.5, dated Jan. 13, 2014.
Chinese Second Office Action, Application No. 200780043725.7, dated Nov. 16, 2011.
EP Communication, Application No. 10817681.9, dated Feb. 26, 2014.
EP Communication, Application No. 07762999.6, dated Aug. 18, 2009.
EP Communication, Application No. 10817681.9, dated Mar. 7, 2013.
EP Communication, Application No. 07867328.2, dated Nov. 6, 2013.
European Supplementary Search Report, Application No. 07762999.6 dated Sep. 4, 2009.
PCT International Preliminary Report on Patentability, PCT/US07/023011 filed Oct. 31, 2007, dated May 14, 2009.
PCT International Preliminary Report on Patentability, PCT/US07/002365 filed Jan. 30, 2007, dated Aug. 5, 2008.
PCT International Preliminary Report on Patentability, PCT/US09/067845 filed Dec. 14, 2009, dated Jun. 23, 2011.
PCT International Preliminary Report on Patentability, PCT/US2009/062317 filed Oct. 28, 2009, dated May 12, 2011.
PCT International Search Report and the Written Opinion, PCT/US07/23011 filed Oct. 31, 2007, dated Sep. 26, 2008.
PCT International Search Report and the Written Opinion, PCT/US11/21127 filed Jan. 13, 2011, dated Apr. 13, 2011.
PCT International Search Report and the Written Opinion, PCT/US10/48227 filed Sep. 9, 2010, dated Nov. 8, 2010.
PCT International Search Report and the Written Opinion, PCT/US07/02365 filed Jan. 30, 2007, dated Dec. 20, 2007.
PCT International Search Report and the Written Opinion, PCT/US09/67845 filed Dec. 14, 2009, dated Aug. 10, 2010.
PCT International Search Report and the Written Opinion, PCT/US09/62317 filed Oct. 28, 2009, dated Mar. 2, 2010.
PCT International Search Report and Written Opinion, Application No. 2013/040181, dated Oct. 25, 2013.
PCT International Search Report and Written Opinion, PCT/US11/21130 filed Jan. 13, 2011, dated Jun. 7, 2011.
Amigo, L. et al., "Enrichment of Canalicular Membrane with Cholesterol and Sphingomyelin Prevents Bile Salt-Induced Hepatic Damage," Journal of Lipid Research, 1999, pp. 533-542, vol. 40.
Aydemir-Koksoy, A. et al., "Ouabain-Induced Signaling and Vascular Smooth Muscle Cell Proliferation," The Journal of Biological Chemistry, 2001, pp. 46605-46611, vol. 276, No. 49.
Bork, "Powers and Pitfalls in Sequence Analysis: The 70% Hurdle", Genome Research, 2000, 10, pp. 398-400.
Brenner, "Errors in Genome Annotation", Trends in Genetics, 1999, 15(4), pp. 132-133.
Cai, T. et al., "Regulation of Caveolin-1 Membrane Trafficking by the Na/K-ATPase," Journal of Cell Biology, 2008, pp. 1153-1169, vol. 182, No. 6.
Chan, et al., Interactions between traditional Chinese medicines and Western therapeutics, Current Opinion in Drug Discovery & Development, 2010, 13 (1), pp. 50-65.
Chen, Y. et al., "Regulation of Intracellular Cholesterol Distribution by Na/K-ATPase," The Journal of Biological Chemistry, May 2009, pp. 14881-14890, vol. 284, No. 22.
Chen, Y., "The N-Terminus of a1 Subunit and Na/K-ATPase-Mediated Signal Transduction," Final Approval of Dissertation, The University of Toledo, College of Medicine, 2009.
Cooper, R. et al., "Medicinal Benefits of Green Tea: Part I. Review of Noncancer Health Benefits," The Journal of Alternative and Complementary Medicine, 2005, pp. 521-528, vol. 11, No. 3.
Cruz, J.C. et al., "Role of Niemann-Pick Type C1 Protein in Intracellular Trafficking of Low Density Lipoprotein-Derived Cholesterol," The Journal of Biological Chemistry, 2000, pp. 4013-4021, vol. 275, No. 6.

(56) References Cited

OTHER PUBLICATIONS

Darra, E. et al., "Protective Effect of Epigallocatechin-3-Gallate on Ischemia/Reperfusion-Induced Injuries in the Heart: STAT1 Silencing Flavenoid," Genes Nutr., 2007, pp. 307-310, vol. 2.
Dmitrieva, R.I. et al., "Cardiotonic Steroids: Potential Endogenous Sodium Pump Ligands with Diverse Function," Exp. Biol. Med., 2002, pp. 561-569, vol. 227, No. 8.
Doerks, et al., "Protein Annotation: Detective Work for Function Prediction", Trends in Genetics, 1998, 14(6), pp. 248-250.
Donovan, et al., The Effect of Age on Digitoxin Pharmacokinetics, Br. J. Clin. Pharmac., 1981.
Elkarch, et al., Marinobufagenin Stimulates Fibroblast Collagen Production and Causes Fibrosis in Experimental Uremic Cardiomyopathy, Hypertension, Jan. 2007.
Elkareh, J. et al., "Marinobufagenin Stimulates Fibroblast Collagen Production and Causes Fibrosis in Experimental Uremic Cardiomyopathy," Hypertension, 2007, pp. 215-224, vol. 49.
El-Okdi, N. et al., "Effects of Cardiotonic Steroids on Dermal Collagen Synthesis and Wound Healing," J. Appl. Physiol., 2008, pp. 30-36, vol. 105.
Haas, M. et al., "SRC-Mediated Inter-Receptor Cross-Talk Between the Na+/K+-ATPase and the Epidermal Growth Factor Receptor Relays the Signal from Ouabain to Mitogen-Activated Protein Kinases," The Journal of Biological Chemistry, 2002, pp. 18694-18702, vol. 277, No. 21.
Hotta, Y. et al., "Positive Inotropic Effect of Purified Green Tea Catechin Derivative in Guinea Pig Hearts: The Measurements of Cellular Ca2+ and Nitric Oxide Release," European Journal of Pharmacology, 2006, pp. 123-130, vol. 552.
Ignatushchenko, et al., Xanthones As Antimalarial Agents: Stage Specificity, Am. J. Trop. Med. Hyg., 62 (1) 2000, pp. 77-81.
Ikeda, I. et al., "Tea Catechins with a Galloyl Moiety Suppress Postprandial Hypertriacylglycerolemia by Delaying Lymphatic Transport of Dietary Fat in Rats," The Journal of Nutrition, 2005, pp. 155-159, vol. 135.
Kabat, M.M. et al., "Cardiotonic Steroids. 5. A Synthesis of Bufadienolides and Cardenolides from 3β-Acetoxy-5-Androsten-17-One via Common Intermediates," J. Org. Chem., 1983, pp. 4248-4251, vol. 48.
Katz, B. et al., "Controlled-Release Drug Delivery Systems in Cardiovascular Medicine," American Heart Journal, 1995, pp. 359-368, vol. 129, No. 2.
Kennedy, D.J. et al., "Central Role for the Cardiotonic Steroid Marinobufagenin in the Pathogenesis of Experimental Uremic Cardiomyopathy," Hypertension, 2006, pp. 488-495, vol. 47.
Khundmiri, S.J. et al., "Ouabine Induces Cell Proliferation through Calcium-Dependent Phosphorylation of Akt (Protein Kinase B) in Opossum Kidney Proximal Tubule Cells," Am. J. Physiol. Cell Physiol., 2006, pp. C1247-C1257, vol. 291.
Kubota, Y. et al., "Safety of Dietary Supplements; Chronotropic and Inotropic Effects on Isolated Rat Atria," Biol. Pharm Bull., 2002, pp. 197-200, vol. 25, No. 2.
Laird, A.D. et al., "Src Family Kinase Activity is Required for Signal Tranducer and Activator of Transcription 3 and Focal Adhesion Kinase Phosphorylation and Vascular Endothelial Growth Factor Signaling in Vivo and for Anchorage-Dependent and -Independent Growth of Human Tumor Cells," Molecular Cancer Therapeutics, May 2003, pp. 461-469, vol. 2.
Lefranc, F. et al., "Targeting the α1 Subunit of the Sodium Pump to Combat Glioblastoma Cells," Neurosurgery, Jan. 2008, pp. 211-222, vol. 62, No. 1.
Liang, M. et al., "Functional Characterization of Src-Interacting Na/K-ATPase Using RNA Interference Assay," The Journal of Biological Chemistry, Jul. 2006, pp. 19709-19719, vol. 281, No. 28.
Melero, et al., A Short Review on Cardiotonic Steriods and Their Aminoguanidine Analogues, Molecules 2000, 5, pp. 51-81.
Newman, R.A. et al., "Cardiac Glycosides as Novel Cancer Therapeutic Agents," Molecular Interventions, Feb. 2008, pp. 36-49, vol. 8, Issue 1.
Ngo, et al., Computational Complexity Protein Structure Prediction, and the Levinthal Paradox, Chapter 14, 1994, pp. 433-440 and 492-495 only.
Paquay, J.B.G. et al., "Protection Against Nitric Oxide Toxicity by Tea," J. Agric. Food Chem., 2000, pp. 5768-5772, vol. 48.
Pedro, et al., Xanthones as Inhibitors of Growth of Human Cancer Cell Lines and Their Effects on the Proliferation of Human Lymphocytes in Vitro, Bioorganic & Medicinal Chemistry 2002, 10, pp. 3725-3730.
Robia, S.L. et al., "Localization and Kinetics of Protein Kinase C-Epsilon Anchoring in Cardiac Myocytes," Biophysical Journal, May 2001, pp. 2140-2151, vol. 80.
Sato, A. et al., "α-Mangostin Induces Ca2+-ATPase-Dependent Apoptosis via Mitochondrial Pathway in PC12 Cells," Journal of Pharmacological Sciences, 2004, pp. 33-40, vol. 95.
Skolnick, et al., From Genes to Protein Structure and Function: Novel Applications of Computational Approaches in the Genomic Era, Trends in Biotech, 2000, 18(1), pp. 34-39.
Susa, M. et al., "Src Inhibitors: Drugs for the Treatment of Osteoporosis, Cancer or Both?" TiPS, 2000, pp. 489-495, vol. 21.
Tian, J. et al., "Changes in Sodium Pump Expression Dictate the Effect s of Ouabine on Cell Growth," The Journal of Biological Chemistry, May 2009, pp. 14921-14929, vol. 284, No. 22.
Tian, J. et al., "Na/K-ATPase Moonlights via Ouabine-Regulated Interaction with Src," Abstract, The FASEB Journal, Mar. 2004, vol. 18, No. 5.
Townsend, P.A. et al., "Epigallocatechin-3-Gallate Inhibits STAT-1 Activation and Protects Cardiac Myocytes from Ischemia/Reperfusion-Induced Apoptosis," The FASEB Journal, 2004, doi: 10.1096/fj.04-1716fje.
Urano, Y. et al., "Transport of LDL-Derived Cholesterol from the NPC1 Compartment to the ER Involves the Trans-Golgi Network and the SNARE Protein Complex," PNAS, Oct. 2008, pp. 16513-16518, vol. 105, No. 43.
Wang, H., "Na+/K+ATPase and Signal Transduction," Final Approval of Dissertation, The University of Toledo, College of Medicine, 2005.
Wells, Additivity of Mutational Effects in Proteins, Biochemisty, 1990, vol. 29, No. 37, pp. 8509-8517.
Yang, et al., Cardiac glycosides inhibit TNF-α/Nf-kB signaling by blocking recruitment of TNF receptor-associated death domain to the TNF receptor, PNAS, Jul. 5, 2005, vol. 102, No. 27, pp. 9631-9636.
Zhang, Z. et al., "Identification of Hyroxyxanthones as Na/K-ATPase Ligands," Molecular Pharmacology, 2010, pp. 961-967, vol. 77, No. 6.
Zhong, et al., 3,4,5,6,-Tetrahydroxyxanthone Protects Against Myocardial Ischemia-Reperfusion Injury in Rats, Cardiovascular Drugs and Therapy, 2004, 18, pp. 279-288.

* cited by examiner

Xanthone

Quercetin

NA/K-ATPASE LIGANDS, OUABAIN ANTAGONISTS, ASSAYS AND USES THEREOF

CROSS-REFERENCE TO RELATED APPLICATIONS

This application is filed under 35 U.S.C §111(a) as a divisional application which claims priority under 35 U.S.C. §119, 35 U.S.C. §120 and the Patent Cooperation Treaty to: parent application U.S. Ser. No. 13/395,700 filed under 35 U.S.C. §371 on Jun. 14, 2012, currently pending; which claims priority to PCT/US2010/048227 filed under the authority of the Patent Cooperation Treaty on Sep. 9, 2010, published; which claims priority to U.S. Provisional Application Ser. No. 61/243,036 filed under 35 U.S.C. §111(b) on Sep. 16, 2009; the disclosures of all priority applications are incorporated herein by reference.

STATEMENT REGARDING FEDERALLY SPONSORED RESEARCH

This invention was made with government support under GM78565, HL36573 and 2007DFA31370 awarded by the National Institutes of Health. The Government has certain rights in the invention.

TECHNICAL FIELD AND INDUSTRIAL APPLICABILITY

The present invention directed to Na/K-ATPase ligands and uses thereof. The present invention is also directed to methods and kits for screening substances for agonist and/or antagonist activity of Na/K-ATPase and for treating or preventing diseases or disorders with substances identified by the screening methods described herein.

BACKGROUND

The Na/K-ATPase, also known as the sodium pump, is a ubiquitous trans-membrane enzyme that transports $Na^+$ and $K^+$ across the plasma membrane by hydrolyzing ATP. It belongs to the family of P-type ATPase that transits between E1 and E2 conformational states during pumping cycles. The functional enzyme is mainly composed of α and β subunits. The α subunit is the catalytic component of the holoenzyme as it contains both the nucleotide and the cation binding sites. Interestingly, studies during the past few years have uncovered many non-pumping functions of Na/K-ATPase such as signal transduction. Specifically, the signaling Na/K-ATPase resides in caveolae and interacts with a number of signaling proteins such as Src, IP3 receptor and caveolin-1. While the interaction between Na/K-ATPase and IP3 receptor facilitates $Ca^{2+}$ signaling, the dynamic association between Na/K-ATPase and Src regulates cellular Src activity and makes it possible for cardiotonic steroids to stimulate protein kinase cascades.

Cardiotonic steroids (CTS) include plant-derived digitalis drugs such as digoxin and ouabain, and vertebrate-derived aglycones such as bufalin and marinobufagenin (MBG).

Although CTS have been considered only as drugs since their discovery, recent studies have identified both ouabain and MBG as endogenous steroids whose production and secretion are regulated by multiple stimuli including angiotensin II and adrenocorticotropic hormone (ACTH). Of the circulating CTS that have been identified and characterized, ouabain remains the most studied. Moreover, the concentrations of CTS were markedly increased under clinical conditions of high salt loading, chronic renal failure (CRF), and congestive heart failure (CHF). Clinically, digitalis drugs can be used to treat congestive heart failure because they have the well-documented inotropic effects on the heart.

Clinically, these steroids can be used to treat congestive heart failure because they have the well-documented inotropic effects on the heart. It is known that the Na/K-ATPase serves as a receptor for these steroids. While binding of CTS to the Na/K-ATPase inhibits the pumping function, it stimulates the signaling function of Na/K-ATPase. For example, binding of ouabain to the Na/K-ATPase/Src receptor complex stimulates Src kinase. The activated Src, in turn, trans-activates receptor tyrosine kinases such as EGF receptor (EGFR) and converts the tyrosine kinase signal to the stimulation of serine/threonine kinases, lipid kinases and lipases as well as increased production of reactive oxygen species (ROS). Interestingly, while inhibition of Na/K-ATPase by CTS is essential for these drugs to increase cardiac contractile function, stimulation of protein kinases and subsequent increases in the production of ROS by these steroids also cause cardiac hypertrophy and fibrosis in animal studies.

Several of the co-inventors herein have discovered "$Na^+$/$K^+$-ATPase Ligand," as disclosed in the pending application U.S. Ser. No. 12/087,976 filed Jul. 31, 2008 (claiming priority from PCT/US07/002,365, filed Jan. 30, 2007 (Pub. No. WO 2007/089688 on Aug. 9, 2007), claiming priority from U.S. Ser. No. 60/763,783 filed Jan. 31, 2006), which applications are expressly incorporated herein by reference.

Several of the co-inventors herein have discovered "$Na^+$/$K^+$-ATPase-Specific Peptide Inhibitors/Activators of Src and Src Family Kinases," as disclosed in the pending application U.S. Ser. No. 12/446,856 filed Apr. 23, 2009 (claiming priority from PCT/US07/023,011, filed Oct. 17, 2007 (Pub. No. WO 2008/054792 on May 8, 2008), claiming priority from U.S. Ser. No. 60/855,482 filed Oct. 16, 2006) which are expressly incorporated herein by reference.

Also, several of the co-inventors herein have discovered "Methods Regulating $Na^+$/$K^+$-ATPase Expression and Uses thereof. As Therapy for Cancer," as disclosed in the application U.S. Ser. No. 61/109,386 filed Oct. 28, 2008, which is expressly incorporated herein by reference.

Also, several of the co-inventors herein have discovered "$Na^+$/$K^+$-ATPase-derived Peptides as Antagonists of CTS and as Therapeutic Agents for Cancer," as disclosed in the pending application U.S. Ser. No. 61/122,205, filed Dec. 12, 2008, which is expressly incorporated herein by reference.

SUMMARY

In a broad aspect there is provided herein a novel class of compounds that are different from cardiotonic steroids (CTS), where such compounds inhibit Na/K-ATPase without activating protein kinases.

In another broad aspect, there is provided herein class of compounds comprising Na/K-ATPase ligands which regulate the ion pumping function of Na/K-ATPase.

In another broad aspect, there is provided herein class of compounds comprising Na/K-ATPase ligands which antagonize CTS-induced activation of protein kinase cascades.

In another broad aspect, there is provided herein one or more assays using Na/K-ATPase ligands.

Various objects and advantages of this invention will become apparent to those skilled in the art from the following detailed description of the preferred embodiment, when read in light of the accompanying drawings.

BRIEF DESCRIPTION OF THE DRAWINGS

The patent or application file may contain one or more drawings executed in color and/or one or more photographs. Copies of this patent or patent application publication with color drawing(s) and/or photograph(s) will be provided by the Patent Office upon request and payment of the necessary fee.

FIG. 7A: The two phase inhibition of both low and high affinity. FIGS. 7B-7C: The dose-response of high affinity inhibition by MB5 (FIG. 7B) and MB7 (FIG. 7C), noting the MB5 is more potent than MB7.

DETAILED DESCRIPTION

Figure 1A:
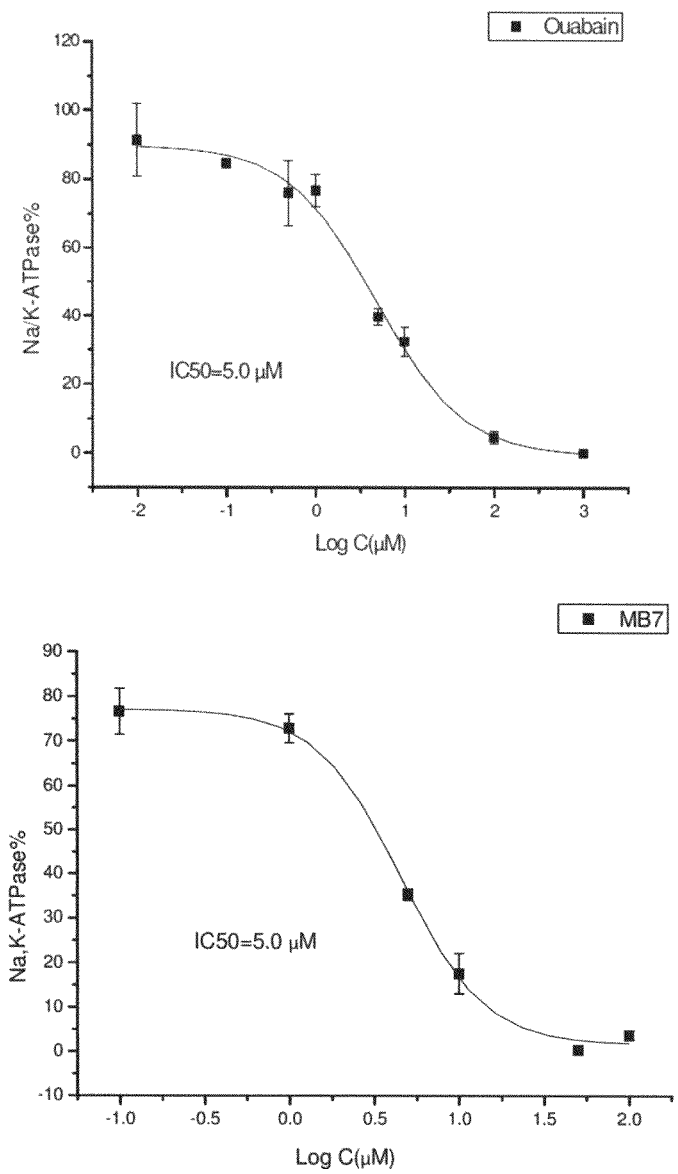
FIG. 1A: Graphs showing concentration curves for ouabain (FIG. 1A-top) and MB7 (3,4,5,6-Tetrahydroxyxanthone) (FIG. 1A-bottom).

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

The present invention is based at least in part, on the inventors' discovery of a novel molecular mechanism of Na/K-ATPase-mediated Src regulation and the identification of hydroxyl xanthone derivatives that: i) reduce both $Na^+$ and ATP affinities on Na/K-ATPase, and ii) act as antagonists that can abolish ouabain-induced activation of kinase cascades.

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. All publications, including patents and non-patent literature, referred to in this specification are expressly incorporated by reference. The following examples are intended to illustrate certain preferred embodiments of the invention and should not be interpreted to limit the scope of the invention as defined in the claims, unless so specified.

Example I

Materials

ATP and ouabain were obtained from Sigma (St. Louis, Mo.). Biomol Green was purchased from BIOMOL (Plymouth Meeting, Pa.). ERK/MAPK (Phospho-Thr202/Tyr204) phosphorylation/translocation cell-based assay kit was purchased from Cayman Chemical Company (Ann Arbor, Mich.). Purified recombinant Src was obtained from Upstate Biotechnology (Lake Placid, N.Y.). Polyclonal anti-Tyr(P)418-Src was obtained from Invitrogen (Camarillo, Calif.). Anti-c-Src (B-12) monoclonal antibody was from Santa Cruz Biotechnology Inc. (Santa Cruz, Calif.). The common chemicals were of the highest purity available. Fresh pig kidneys were purchased from a nearby slaughterhouse, and stored at −80° C. until used for enzyme preparation.

High Throughput Screen Assay:

The chemical library used for screening in the present study contained 2600 structurally diverse, drug-like, naturally occurring organic compounds or their semi-synthetic derivatives. Stock compounds were prepared in 96-well plates at 10 mg/ml in DMSO.

The purified Na/K-ATPase was prepared from pig kidney. The specific activities of Na/K-ATPase of various kidney preparations were in the range of 900-1,200 µmol/mg/h, which were greater than 95% of the total ATPase activity. The high throughput screen is conducted in a 96-well format with the final reaction volume of 100 µl containing the following components: 100 mM NaCl, 20 mM KCl, 1 mM $MgCl_2$, 1 mM EGTA, 20 mM Tris-HCl (pH 7.4) and 0.2 µg of purified Na/K-ATPase. After compounds were added, mixtures were incubated for 15 min at 37° C. for 15 min and reaction was initiated by adding 2 mM ATP.Mg mixture.

Reactions were carried out for 15 min and then stopped by the addition of 100 µl ice-cold trichloroacetic acid. Reaction mixtures were cleared by centrifugation, and assayed for released phosphate using the BIOMOL GREEN™ Reagent according to the manufacturer's instructions. In addition, the control Na/K-ATPase activity was measured in the presence and absence of 1 mM ouabain, and taken as 100%. Furthermore, 5 µM ouabain and 0.1% of DMSO were included in each plate as a positive and a vehicle control, respectively. Control experiments showed that ATP hydrolysis catalyzed by the Na/K-ATPase was in linear range within 30 min of incubation under the above experimental conditions.

Cell Culture:

The pig kidney epithelia cells (LLC-PK1 cells) and human lung cancer cells (A549 cells) were obtained from ATCC and maintained in Dulbecco's modified Eagle's medium (DMEM) in the presence of 10% FBS, 100 units/ml penicillin, and 100 µg/ml streptomycin in a 5% $CO_2$ humidified incubator. To eliminate the confounding effect of growth factors in the serum, cells were serum starved for 24 h before experiments unless otherwise indicated.

Western Blot Analysis:

Cells were washed with PBS and solubilized in ice-cold RIPA buffer containing 1% Nonidet P-40, 1% sodium deoxycholate, 150 mM NaCl, 1 mM EDTA, 1 mM phenylmethylsulfonyl fluoride, 1 mM sodium orthovanadate, 1 mM NaF, 10 µg/ml aprotinin, 10 µg/ml leupeptin, and 50 mM Tris-HCl (pH 7.4) as previously described (13). Cell lysates were then cleared by centrifugation at 14,000 rpm, and supernatants were used for protein assay and subjected to Western blot analysis. Samples were separated on SDS-PAGE (50 µg/lane) and transferred to a cellulose membrane. Membranes were blocked with 3% non-fat dried milk for total Src and ERK or 1% BSA plus 1% non-fat dried milk for phosphorylated Src and ERK in TBST (Tris-HCl 10 mM, NaCl 150 mM, Tween 20, 0.1%; pH 8.0) for 1 h at room temperature and then probed with specific antibodies. Protein signals were detected using an ECL kit and quantified using a Bio-Rad GS-670 imaging densitometer.

Assay for the Activation of Receptor Na/K-ATPase/Src Complex:

The activity of receptor Na/K-ATPase/Src complex was assayed. Briefly, the purified Src (4.5 U) was incubated with 2 µg of the purified Na/K-ATPase in phosphate-buffered saline (PBS) for 30 min at 37° C. Afterward, the Na/K-ATPase/Src complex was exposed to ouabain or MB7 for 10 min. Reaction was initiated by addition of 2 mM ATP/$Mg^{2+}$, continued for 5 min at 37° C. and was stopped by addition of SDS sample buffer. The activation of Src was measured by Western blot using anti-pY418 antibody. Total Src was also probed for loading control.

Confocal Imaging and Immunocytochemistry:

LLC-PK1 cells grown on coverslips were serum starved for 24 h and treated with MB7 or ouabain for different times Immunostaining of p-ERK was performed using the commercial available ERK/MAPK (Phospho-Thr202/Tyr204) Phosphorylation/Translocation Cell-Based Assay Kit according to the manufacturer's instructions. The signals were detected by a Leica confocal microscope. Leica confocal software was used for data analysis.

Data Analysis:

Data are given as mean±S.E. Statistical analysis was performed using the Student's t test and significance was accepted at $p<0.05$.

Results for Example I

High Throughput Screening of Na/K-ATPase Inhibitors

To screen a chemical library for Na/K-ATPase inhibitors, the inventors herein developed a 96-well format assay.

As depicted in FIG. 1A, ouabain, as a positive control, produced a dose-dependent inhibition of Na/K-ATPase. On the other hand, DMSO, the vesicle, showed no effect on the Na/K-ATPase activity when used at concentration below 1% of reaction volume (data not shown). The apparent $IC_{50}$ for ouabain was about 5 µM, comparable to what was reported. The same assay was used to test a total of 2600 compounds at the final concentration of 10 µg/ml. This concentration was adapted because a majority of compounds has a molecular mass around 200, thus being tested around 50 µM, ten times of $IC_{50}$ of ouabain. Ouabain (5 µM) was used as a positive control whereas 0.1% DMSO was used as a negative control in each 96-well plate. Assays were conducted in duplicate and the compound that produced at least 25% of inhibition of Na/K-ATPase was identified as a positive hit. Under these experimental conditions, we found a total of 15 positive compounds (Table I below) that include several well-known Na/K-ATPase inhibitors (myricetin, oligomycin, resibufogenin and cinobufagin.

TABLE I

Na/K-ATPase inhibitors identified by high throughput screen

| Sample No. | Name | Formula |
| --- | --- | --- |
| 2006BD3 | Metacycline hydrochloride | $C_{22}H_{22}N_2O_8 \cdot HCl$ |
| 2006BC4 | Mitomycin | $C_{15}H_{18}N_4O_5$ |
| 2008BB8 | Tyrothricin | Mixture |
| 2006BC9 | 4-Epitetracycline | $C_{22}H_{24}N_2O_8$ |
| 2018BF7 | Myricetin | $C_{15}H_{10}O_8$ |
| 2021BG2 | Domiphen bromide | $C_{22}H_{40}NO \cdot Br$ |
| 2035BD1 | Resibufogenin | $C_{24}H_{32}O_4$ |
| 2035BA5 | Cinobufagin | $C_{26}H_{34}O_6$ |
| 2036BF1 | Oligomycin | $C_{45}H_{74}O_{11}$ |
| MB1 | 1,3-Dihydroxyxanthone | $C_{13}H_8O_4$ |

TABLE I-continued

Na/K-ATPase inhibitors identified by high throughput screen

| Sample No. | Name | Formula |
|---|---|---|
| MB2 | 3,4-Dihydroxyxanthone | $C_{13}H_8O_4$ |
| MB3 | 1,3,5-Trihydroxyxanthone | $C_{13}H_8O_5$ |
| MB5 | 3,4,5-Trihydroxyxanthone | $C_{13}H_8O_5$ |
| MB6 | 1,3,5,6-Tetrahydroxyxanthone | $C_{13}H_8O_6$ |
| MB7 | 3,4,5,6-Tetrahydroxyxanthone | $C_{13}H_8O_6$ |

Figure 1B:
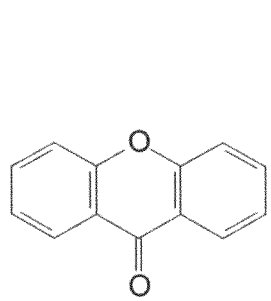
FIG. 1B: Chemical structures of xanthone (left) and quercetin (right).
Figure 1B:
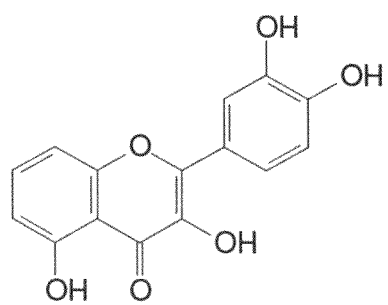

Identification of Hydroxyxanthones as a New Class of Na/K-ATPase Ligands:

Among the fifteen positive hits, many are polyphenolic compounds including six hydroxyl xanthone derivatives (MB1 to MB7) (Table 1). Structurally, they are similar to the well-characterized polyphenolic compounds such as quercetin (FIG. 1B). The inventors herein then determined the inhibitory properties of these hydroxyxanthones. Because MB7 was the most potent inhibitor of this group (Table II below), it was used in the following studies.

TABLE II

Structure and Activity Relationship of Xanthone Derivatives

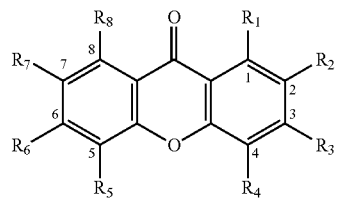

| Sample No. | $R_1$ | $R_2$ | $R_3$ | $R_4$ | $R_5$ | $R_6$ | $R_7$ | $R_8$ | IC50 (µM) |
|---|---|---|---|---|---|---|---|---|---|
| MB1 | OH | H | OH | H | H | H | H | H | >100 |
| MB2 | H | H | OH | OH | H | H | H | H | >100 |
| MB3 | OH | H | OH | H | OH | H | H | H | 65 |
| MB5 | H | H | OH | OH | OH | H | H | H | 10 |
| MB6 | OH | H | OH | H | OH | OH | H | H | 60 |
| MB7 | H | H | OH | OH | OH | OH | H | H | 5 |
| MB8 | H | H | $OCH_3$ | $OCH_3$ | H | $OCH_3$ | H | H | >100 |
| 2027BA1 | OH | H | $OCH_3$ | H | H | H | OH | $OCH_3$ | >100 |
| 2027BA2 | OH | H | $OCH_3$ | H | H | H | $OCH_3$ | OH | >100 |
| C-017 | $OCH_3$ | $OCH_3$ | $OCH_3$ | H | H | H | $OCH_3$ | H | >100 |

Figure 2A:
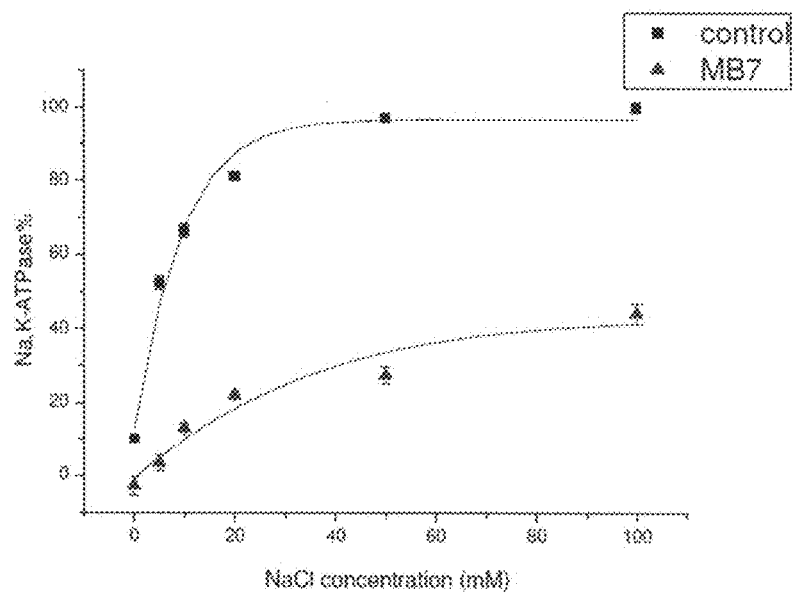
FIGS. 2A-2B: Effects of MB7 on $Na^+$ (FIG. 2A) and ATP (FIG. 2B) dependence. Na/K-ATPase activity was measured as described in "Experimental Procedures" as a function of $Na^+$ or ATP concentration. MB7 was used at 10 µM.
Figure 2B:
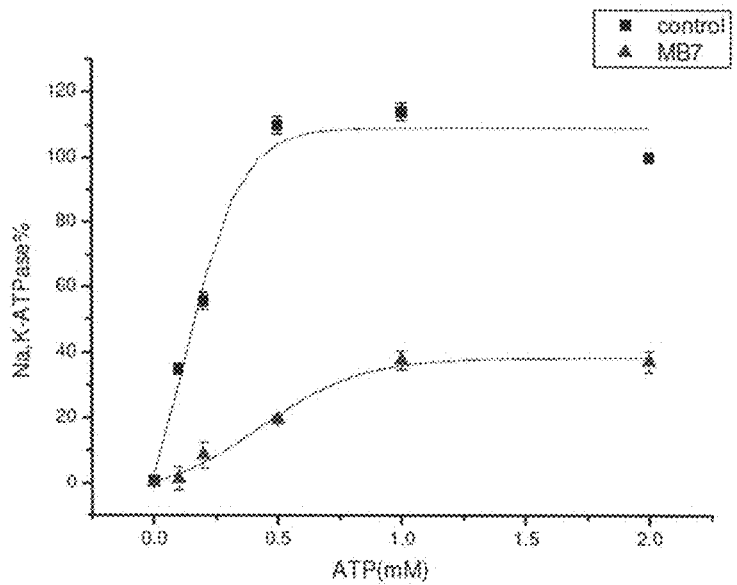

In the experiments depicted in FIG. 1A, the dose-response curves of MB7 were compared with ouabain. Like ouabain, MB7 exhibited a dose-dependent inhibition of Na/K-ATPase. The apparent $IC_{50}$ (5 µM) is comparable to that of ouabain. However, when effects of MB7 on the substrate dependence were determined, MB7, unlike ouabain, reduced both $Na^+$ and ATP affinities of Na/K-ATPase (FIG. 2A and FIG. 2B). On the other hand, changes in $K^+$ concentration showed no effect on MB7-induced inhibition of Na/K-ATPase (data not shown), but antagonized ouabain-induced inhibition. Furthermore, 10 µM MB7 produced 58±6% inhibition of Na-ATPase as did on Na/K-ATPase. Taken together, the data show that hydroxyxanthones inhibit the Na/K-ATPase through a different mechanism from that of ouabain.

To determine the structure-activity relationship, the dose-response curves of xanthone, six hydroxyxanthones and several methylated hydroxyxanthone derivatives were compared. As depicted in Table II, while xanthone failed to inhibit the Na/K-ATPase activity, an increase in the number of phenolic groups increased the efficacy and potency of hydroxyxanthones (e.g., comparing MB2 with MB5, Table II). Consistently, full or partial methylation was able to reduce the inhibitory effect of hydroxyxanthones on the Na/K-ATPase (e.g., comparing MB5 with MB8). Also, when phenolic groups were positioned near the oxygen in the pyrone ring (i.e., at the position 4 and 5), they had more effect on the potency of these compounds (e.g., comparing MB3 with MB5).

MB7 Fails to Activate the Receptor Na/K-ATPase/Src Complex:

The Na/K-ATPase interacts with Src kinase to form a functional receptor complex for ouabain to activate protein kinase cascades.

Figure 3:
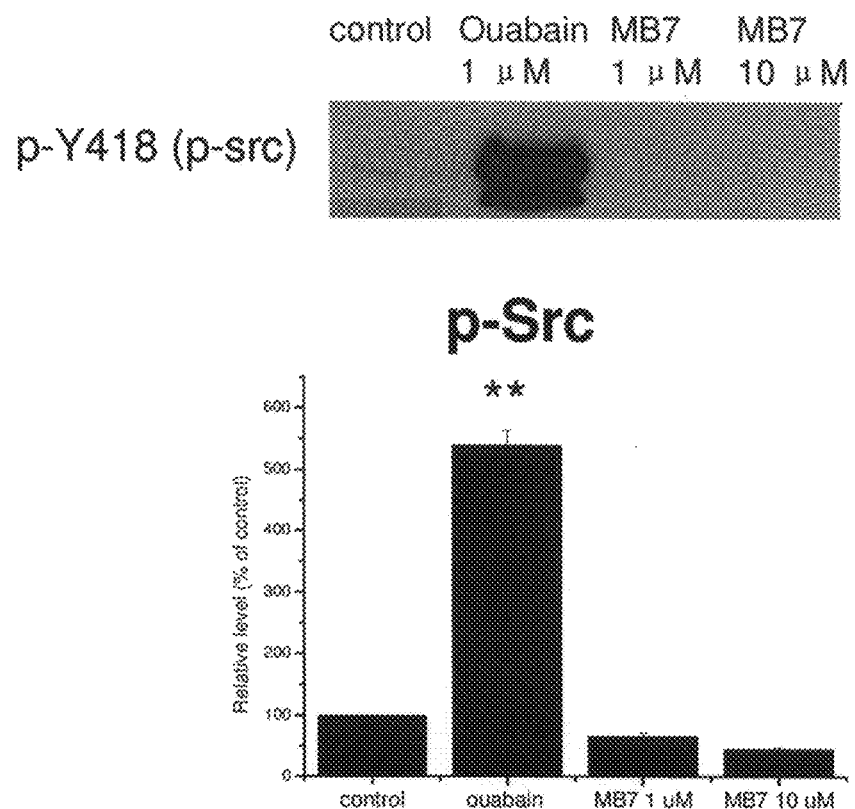
FIG. 3: Effects of MB7 and ouabain on receptor Na/K-ATPase/Src complex. The purified Na/K-ATPase (2 µg) and purified Src were incubated in the presence of either 10 µM ouabain or 1 and 10 µM MB7 for 15 min and assayed for Src activation as described in "Experimental Procedures". Values are mean SE of at least three independent experiments. **$p<0.01$ compared with control.

To determine whether MB7 works as ouabain, capable of activating protein kinases, the inventors herein first measured the effect of MB7 on Src activity using the reconstituted Na/K-ATPase/Src complex. Ouabain (10 µM) was used as a positive control. As depicted in FIG. 3, the Na/K-ATPase inhibited Src. Surprisingly, however, the addition of ouabain, but not MB7, stimulated the Na/K-ATPase-associated Src in the test tube. This discovery now shows that MB7 can inhibit the ATPase activity without stimulating the receptor function of Na/K-ATPase.

Figure 4A:
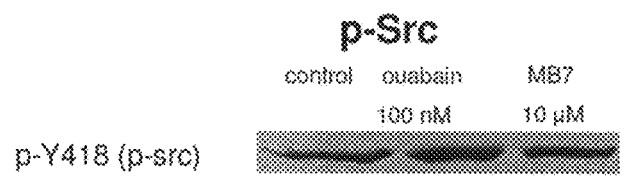
FIG. 4A: Effects of MB7 and ouabain on Src and ERKs. A549 cells were treated with ouabain or MB7 for 10 min and cell lysates (50 µg/lane) were separated by SDS-PAGE and analyzed for Src activation as in FIG. 3. The values are mean±S.E. from four separate experiments. *, $p<0.05$ versus control.

To verify the above results, the effect of MB7 on Src and ERKs in cultured cells was measured. Ouabain was again used as a positive control. As shown in FIG. 4A, while 100 nM ouabain stimulated Src in A549 cells, MB7 up to 10 µM failed to do the same.

Figure 4A:
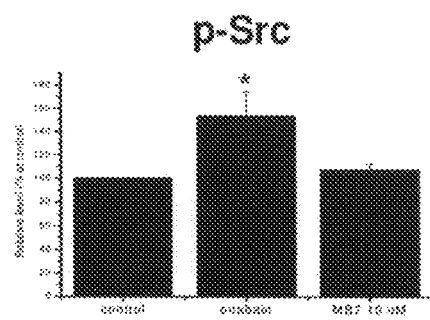
Figure 4B:
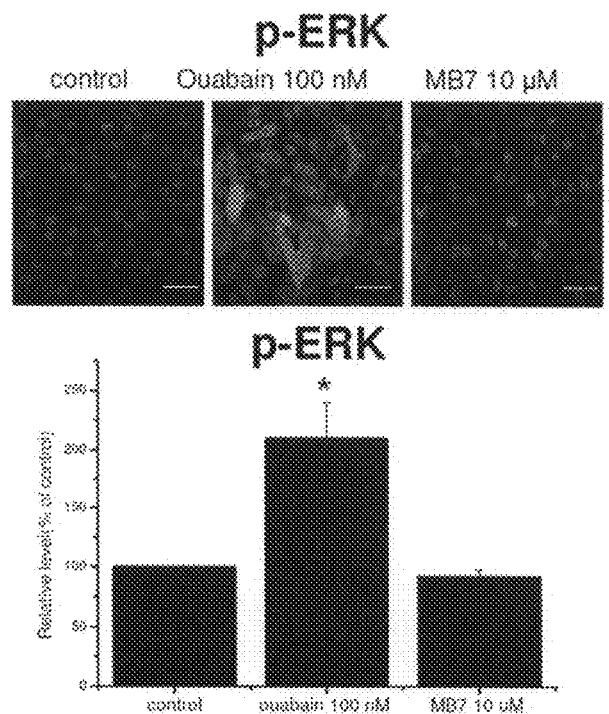
FIG. 4B: LLC-PK1 cells were treated with MB7 or ouabain for 10 minutes and were immunostained with the ERK/MAPK (Phospho-Thr202/Tyr204) Phosphorylation/Translocation Cell-Based Assay Kit according to the manufacturer's instructions. The images were collected as described under "Experimental Procedures." The scale bar represents 50 µM. Images from a representative experiment are shown. The quantitative data of p-ERK were collected from 40 different fields in three independent experiments and expressed as mean±S.E. *, $p<0.05$ versus control.

To further confirm, LLC-PK1 cells were treated with either 100 nM ouabain or different concentrations of MB7. Ouabain stimulated Src and subsequently the ERK cascade in LLC-PK1 cells. Now, it is shown herein that ouabain increased cellular amount of active ERKs as detected by immunostaining (FIG. 4B). However, under the same experimental conditions, MB7 (from 100 nM to 10 µM) failed to affect cellular ERK activity.

Discussion of Example I

An effective high throughput screen assay was used to identify 15 Na/K-ATPase inhibitors that represent several structurally divergent classes of compounds. In addition, the newly identified inhibitors were differentiated from other known inhibitors, such as ouabain and oligomycin, by assessing their effects on substrate dependence of the Na/K-ATPase. The newly identified xanthone derivatives, unlike ouabain, only inhibit the ATPase activity, but do not activating the receptor Na/K-ATPase/Src complex.

Xanthone Derivatives as a New Class of Na/K-ATPase Inhibitors:

According to the Albers-Post reaction scheme, the Na/K-ATPase transits from E1 to E2 state via multiple conformational changes. While $Na^+$ favors the E1 state, $K^+$ promotes the E2 state. Over the years, several classes of organic Na/K-ATPase inhibitors have been identified. They inhibit the Na/K-ATPase by stabilizing the enzyme at different conformational states. For example, CTS bind and stabilize the Na/K-ATPase at the E2P whereas oligomycin prevents E1P to E2P transition.

In comparison, the inventors herein show that the novel ligand, MB7, appears to reduce the formation of E1NaATP because it decreases the apparent affinity of both $Na^+$ and ATP without affecting the $K^+$ sensitivity of the Na/K-ATPase. Interestingly, xanthones share the similar chemical structures as flavonoids since they both share the same benzopyrone in their structure (FIG. 1B). Moreover, quercetin and myricetin are well known potent Na/K-ATPase inhibitors. However, unlike MB7, they do not reduce the affinity of Na/K-ATPase towards either $Na^+$ or ATP.

The fusion of a benzene ring to benzopyrone completely alters the interaction characteristics of xanthones with the Na/K-ATPase, which underlines the specificity of xanthone derivative-induced inhibition of Na/K-ATPase.

In addition, the data presented in Table II show the importance of phenolic groups in xanthone derivative-induced inhibition of Na/K-ATPase. The parent compound xanthone has no phenolic group attached to benzene rings and it showed no detectable inhibition of Na/K-ATPase. While tetrahydroxyxanthone is the most potent inhibitor, dihydroxyxanthones barely affect the ATPase activity.

While not wishing to be bound by theory, the inventors herein now believe that, since the Na/K-ATPase shares many common features with other P-type ATPases, the newly identified xanthone derivatives described herein may also affect other ion pumps. The inventors herein now also believe that other positive hits such as mitomycin and 4-epitetracycline, are likely to represent another class of new ligands.

The xanthone derivatives compounds have different chemical structures from the known Na/K-ATPase inhibitors, and are now believed by the inventors herein to be a new class of Na/K-ATPase inhibitors that work through a different mechanism.

MB7 does not Activate the Receptor Na/K-ATPase/Src Complex:

The Na/K-ATPase binds Src both in vitro and in vivo. This association regulates cellular Src activity by keeping Src in an inactive state (11). Moreover, the formation of Na/K-ATPase/Src complex produces a functional receptor for ouabain to stimulate the pump-associated Src, which subsequently assembles and activates multiple down stream protein kinase cascades including the ERKs, as shown in FIG. 4.

In contrast to ouabain, the binding of MB7 to the Na/K-ATPase/Src complex in vitro failed to activate Src (FIG. 3). Consistently, it had no effect on cellular Src and ERK activity when MB7 was applied to cultured cells. This discovery shows that MB7, unlike ouabain, fails to alter the conformation of Na/K-ATPase in a way so that the Src kinase domain can be released from the Na/K-ATPase. The MB7 inhibits Na/K-ATPase in a different way from that of ouabain.

Perspectives:

The name xanthone designates a group of secondary metabolites normally found in a restricted assembly of plants, fungi and lichens. The xanthones from plants appear to be associated mainly with the families Polygalaceae, Guttiferae, Moraceae and Gentianaceae. These plants have been widely used in traditional Chinese medicine. For example, Yuanzhi, root of *Polygala tenuifolia* Willd. or *Polygala sibirica* L., is extensively used for variety of medical conditions. As phenolic compounds, xanthones have been described for their antioxidant properties. These properties have been implicated in their anti-inflammatory and chemopreventive actions. One of xanthones, dimethylxanthenone-4-acetic acid, is currently undergoing clinical trials as an antitumor agent.

As a new class of Na/K-ATPase inhibitors, the xanthones may also increase cardiac contractile function. Such xanthones are of great value because they do not stimulate the receptor Na/K-ATPase/Src complex. This becomes important since stimulation of Na/K-ATPase-mediated signal transduction by either endogenous or exogenous CTS alters cardiac growth and induces cardiac fibrosis.

Therefore, MB7 and its analogs are now believed to be especially useful to improve contractile function without precipitating cardiac hypertrophy and/or fibrosis that is often seen under clinical conditions of congestive heart failure.

Example II

Materials

ATP and ouabain were obtained from Sigma (St. Louis, Mo.). Biomol Green was purchased from BIOMOL (Plymouth Meeting, Pa.). ERK/MAPK (Phospho-$Thr^{202}/Tyr^{204}$) phosphorylation/translocation cell-based assay kit was purchased from Cayman Chemical Company (Ann Arbor, Mich.). Polyclonal anti-Tyr$(P)^{418}$-Src was obtained from Invitrogen (Camarillo, Calif.). Anti-c-Src (B-12) monoclonal antibody was from Santa Cruz Biotechnology Inc. (Santa Cruz, Calif.). The common chemicals were of the highest purity available. Fresh pig kidneys were purchased from a nearby slaughterhouse, and stored at −80° C. until used for enzyme preparation.

Na/K-ATPase Purification and Activity Assay:

The purified Na/K-ATPase was prepared from pig kidney. The specific activities of Na/K-ATPase of various kidney preparations were in the range of 900-1,200 µmol/mg/h, which were greater than 95% of the total ATPase activity. The Na/K-ATPase assay was conducted in the following reaction buffer with the final volume of 500 µl: 100 mM NaCl, 20 mM KCl, 1 mM $MgCl_2$, 1 mM EGTA, 20 mM Tris-HCl (pH 7.4) and 1 µg of purified Na/K-ATPase. After compounds were added, mixtures were incubated for 15 min at 37° C. for 15 min and reaction was initiated by adding 2 mM ATP.Mg mixture. Reactions were carried out for 15 min and then stopped by the addition of 300 µl ice-cold trichloroacetic acid. Reaction mixtures were cleared by centrifugation, and assayed for released phosphate using the BIOMOL GREEN™ Reagent according to the manufacturer's instructions. Control experiments showed that ATP hydrolysis catalyzed by the Na/K-ATPase was in linear range within 30 min of incubation under the above experimental conditions.

Cell Culture:

The pig kidney epithelia cells (LLC-PK1 cells) and human lung cancer cells (A549 cells) were obtained from ATCC and maintained in Dulbecco's modified Eagle's medium (DMEM) in the presence of 10% FBS, 100 units/ml penicillin, and 100 µg/ml streptomycin in a 5% CO2 humidified incubator. To eliminate the confounding effect of growth factors in the serum, cells were serum starved for 24 h before experiments unless otherwise indicated.

Src Activity Assay and Western Blot Analysis:

The protocol to measure the effects of Na/K-ATPase and its ligands on Src activity by Western blotting Src pY 418 phosphorylation were followed. To prepare cell lysates for Western analysis, cells were washed with PBS and solubilized in ice-cold RIPA buffer containing 1% Nonidet P-40, 1% sodium deoxycholate, 150 mM NaCl, 1 mM EDTA, 1 mM phenylmethylsulfonyl fluoride, 1 mM sodium orthovanadate, 1 mM NaF, 10 µg/ml aprotinin, 10 µg/ml leupeptin, and 50 mM Tris-HCl (pH 7.4). Cell lysates were then cleared by centrifugation at 14,000 rpm, and supernatants were used for protein assay and subjected to Western blot analysis. Samples were separated on SDS-PAGE (50 µg/lane) and transferred to a cellulose membrane. Membranes were blocked with 3% non-fat dried milk for total Src and ERK or 1% BSA plus 1% non-fat dried milk for phosphorylated Src and ERK in TBST (Tris-HCl 10 mM, NaCl 150 mM, Tween 20, 0.1%; pH 8.0) for 1 h at room temperature and then probed with specific antibodies. Protein signals were detected using an ECL kit and quantified using a Bio-Rad GS-670 imaging densitometer.

Confocal Imaging and Immunocytochemistry:

LLC-PK1 cells grown on coverslips were serum starved for 24 h and treated with MB5 or ouabain for different times Immunostaining of p-ERK was performed using the commercial available ERK/MAPK (Phospho-Thr202/Tyr204) Phosphorylation/Translocation Cell-Based Assay Kit according to the manufacturer's instructions. The signals were detected by a Leica confocal microscope. Leica confocal software was used for data analysis.

Data Analysis:

Data are given as mean±S.E. Statistical analysis was performed using the Student's t test and significance was accepted at $p<0.05$.

Results for Example II

The Na/K-ATPase Regulates Src in a Conformation-Dependent Manner

Figure 5A:
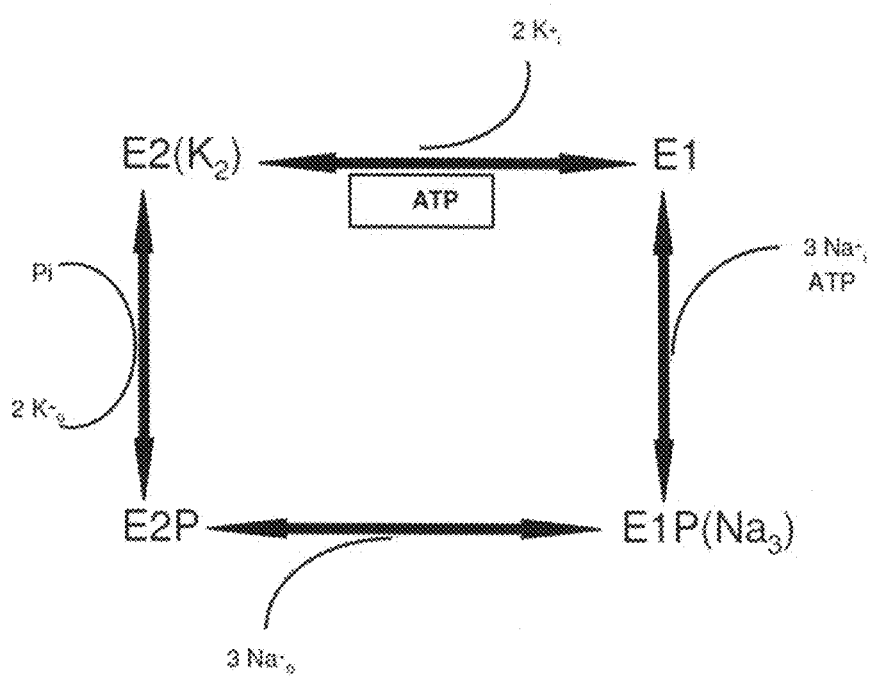
FIG. 5A: Albers-Post Scheme for the Na/K-ATPase pumping cycle.

A large number of Na/K-ATPase interacts directly with Src kinase in life cells. The interaction involves at least two pairs of protein domains. Specifically, the second cytosolic domain of µl subunit interacts with the Src SH2 and the nucleotide binding (N) domain associates with the Src kinase domain. During the pumping cycle, the Na/K-ATPase undergoes E1 to E2 conformational transition (FIG. 5A) where the N domain closes up and the A domain rotates to dock onto the N domain (FIG. 5B).

Figure 5B:
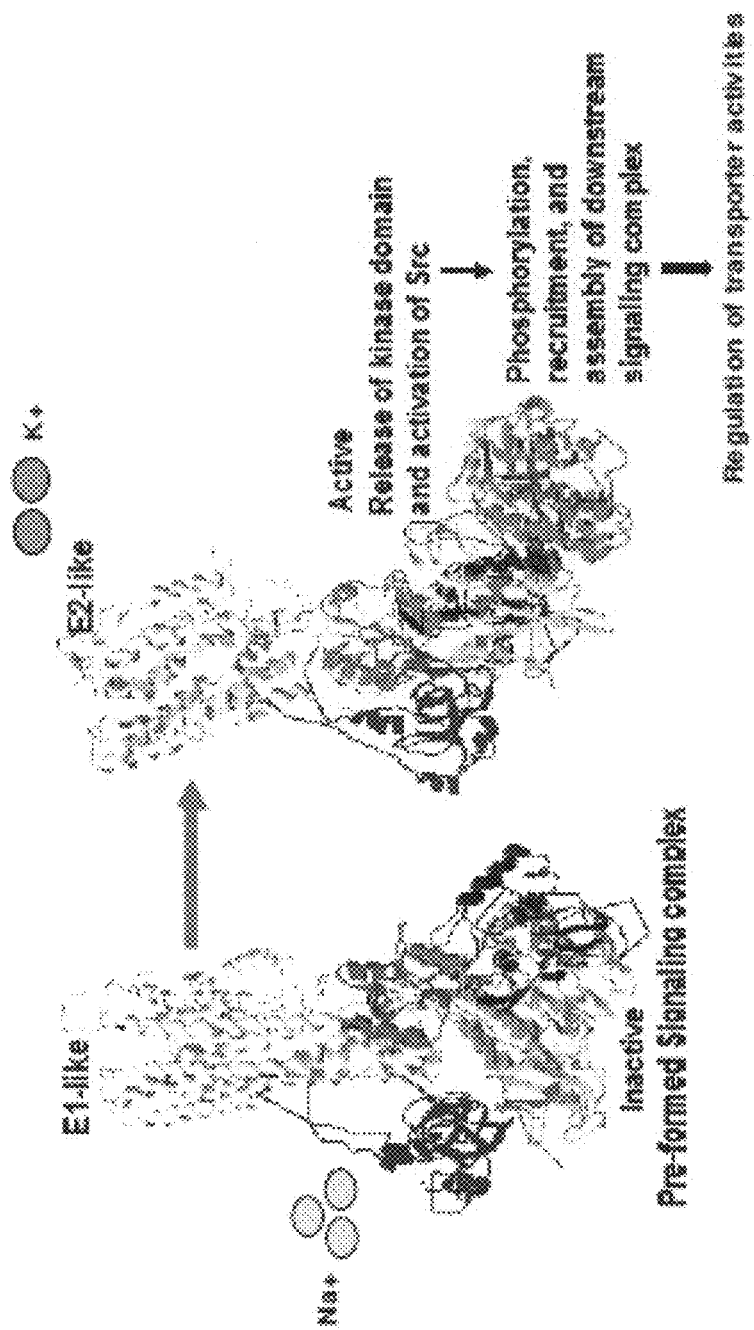
FIG. 5B: Modeling of the Na/K-ATPase/Src interaction. The A domain (N-terminus and CD2) in Na/K-ATPase was labeled in blue, P domain in green, N domain in black. The SH2 domain of Src was labeled in orange, kinase domain in light blue

Structure modeling shows that the location of and the space between the A and N domains only at the E1 state are suitable for the µl subunit to bind both the SH2 and the kinase domains simultaneously (FIG. 5B). Thus, it is now believed by the inventors herein that, while the E1 Na/K-ATPase inhibits Src, the Na/K-ATPase-associated Src must be active when the enzyme is at the E2 conformation.

Figure 6A:
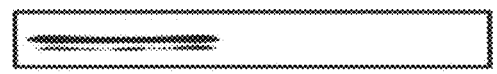
FIG. 6A: Effects of changes in $Na^+$ and $K^+$ concentrations on the receptor Na/K-ATPase/Src activity. Purified Na/K ATPase (2 ug) was resuspended in Tris/HCl (pH7.4) buffer with indicated ion concentrations and incubated with purified c-Src for 15 minutes. Then 3 mM $Mg^{2+}$/ATP was added to the reaction mixture and incubated for another 10 minutes. The samples were analyzed by Western Blot. Values are mean±SE of four separate experiments
Figure 6A:
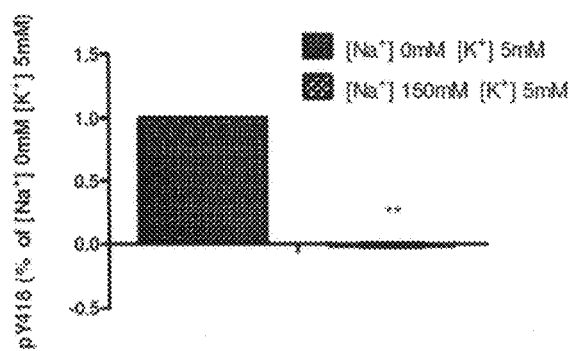
Figure 6B:
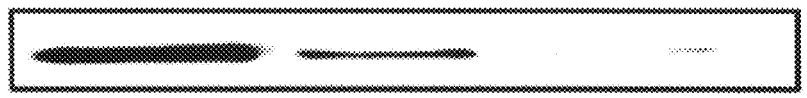
FIG. 6B: Effects of $K^+$ on the receptor Na/K-ATPase/Src activity. The assay was conducted as in FIG. 6A in the presence of 15 mM NaCl and different concentrations of KCl as indicated. A representative Western blot of three separate experiments is shown.
Figure 7A:
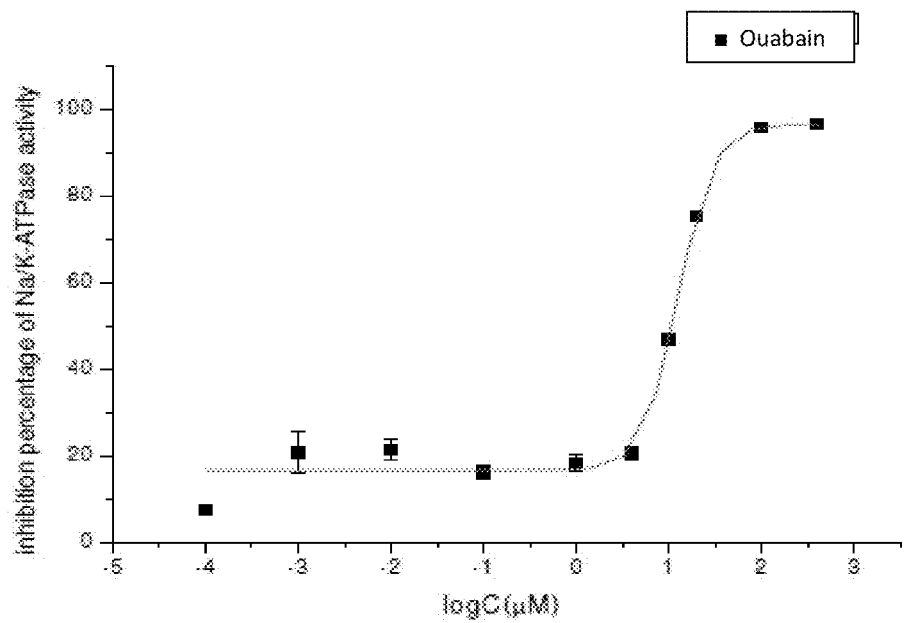
FIGS. 7A-7C: Dose-dependent inhibition of Na/K-ATPase by MB5.
Figure 7B:
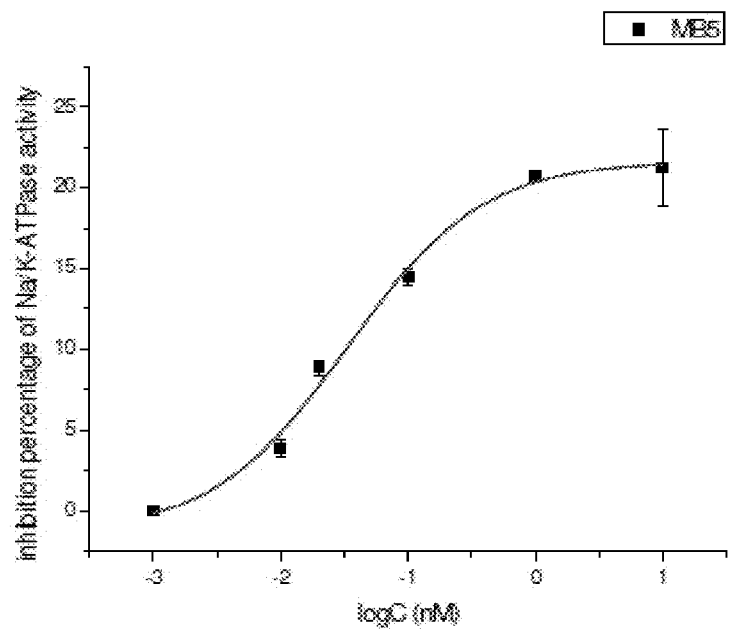
Figure 7C:
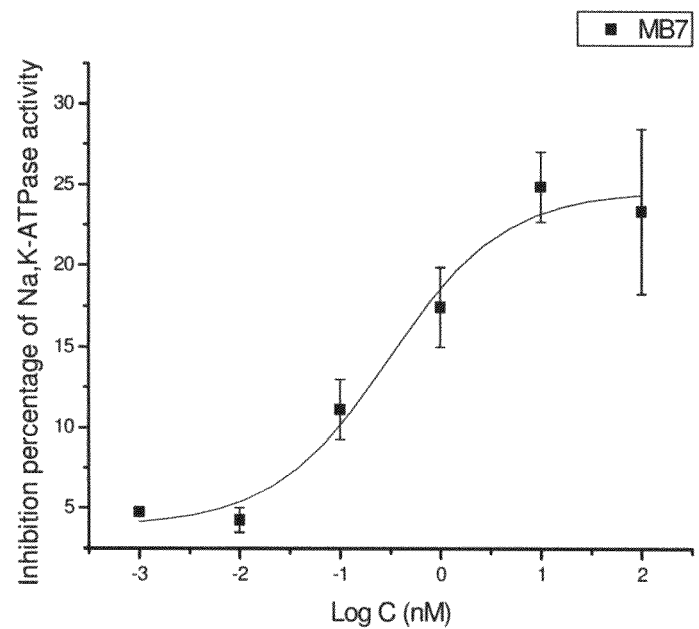

Indeed, when the majority of Na/K-ATPase is stabilized in the E2 conformation by incubating the enzyme in Na$^+$-free and 5 mM buffer (47), the Na/K-ATPase-associated Src became fully active (FIG. 6A). Consistently, addition of 150 mM Na$^+$ to this reaction buffer destabilized the E2 Na/K-ATPase, which resulted in the inactivation of Src (FIG. 6A). Moreover, reduction of K$^+$ from 5 mM to 0 caused a gradual activation of Src (FIG. 6B). These results show that the interaction between the Na/K-ATPase and Src can be regulated by changes in the conformational state of Na/K-ATPase. Furthermore, inhibition of E1 to E2 conformational transition of Na/K-ATPase can be used to antagonize ouabain-induced Src activation.

Xanthone Derivatives are Potent Na/K-ATPase Inhibitors and Prevents Ouabain from Binding to the Na/K-ATPase:

New xanthone derivatives as a class of new Na/K-ATPase ligands that stabilize the Na/K-ATPase in the E1 conformation are described in EXAMPLE I.

Figure 8:
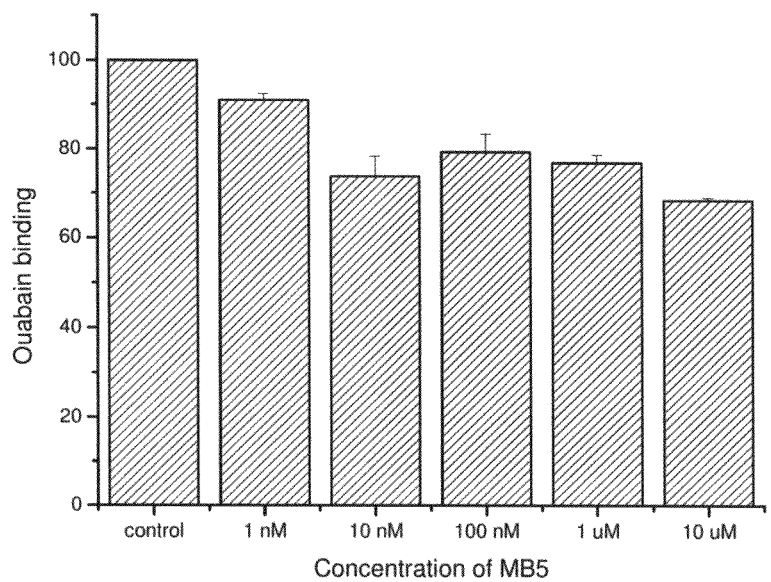
FIG. 8: Effects of MB5 on ouabain binding to the purified Na/K-ATPase. The purified Na/K-ATPase (2 µg) was incubated with 20 nM $^3$H ouabain in the presence of different concentrations of MB5.

As depicted in FIGS. 1 and 7A-C, hydroxyxanthones exhibited two phases of inhibition of Na/K-ATPase activity. The high affinity inhibition by MB5 occurs at sub-nM concentrations (IC50 of 40 pM), producing about 25% inhibition of the ATPase activity, whereas low affinity binding produces 100% inhibition at about 50 µM. It is of interest to note that while MB5 is more potent than MB7 at the high affinity site, it has lower potency at low affinity site. Because ouabain prefers to bind the E2 Na/K-ATPase, stabilization of the Na/K-ATPase at the E1 state by MB5 can be used to antagonize ouabain binding. Indeed, as depicted in FIG. 8, MB5 produced a dose-dependent inhibition of ouabain binding to the purified Na/K-ATPase. The significant inhibition was detected at 0.1 nM and maximal inhibition of 30% was reached when the Na/K-ATPase was exposed to 10 µM MB5.

MB5 Antagonizes Ouabain-, but not EGF and Dopamine, Induced Activation of Protein Kinases:

Ouabain stimulates protein kinase cascades via a Src-dependent pathway in LLC-PK1 cells. To determine whether MB5 can antagonize ouabain-induced signal transduction, treated LLC-PK1 cells were pre-treated with different concentrations of MB5 for 15 min and then exposed to ouabain or other stimuli.

As shown in FIGS. 9A-9D, while ouabain (1 nM and 100 nM) stimulated ERKs in a time and concentration-dependent manner, MB5 at 1 nM was able to significantly reduce ouabain-induced activation of ERKs. Moreover, when MB5 was used at 10 µM, it completely blocked the effect of ouabain on ERKs in LLC-PK1 cells.

Figure 9A:
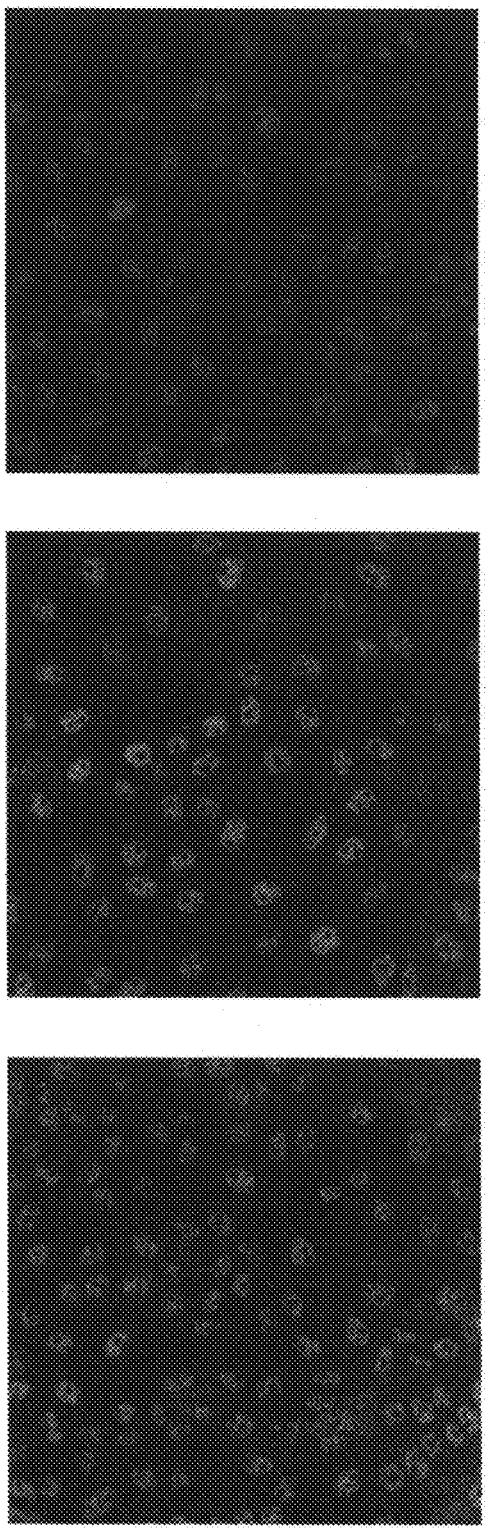
FIG. 9A: Effects of MB5 on ERKs. LLC-PK1 cells were exposed to different concentrations of MB5 (1 nM, 10 µM) for 10 min, and then assayed for active ERKs as described in "Experimental Procedures". A representative set of images is shown. The same experiments were repeated three times.
Figure 9B:
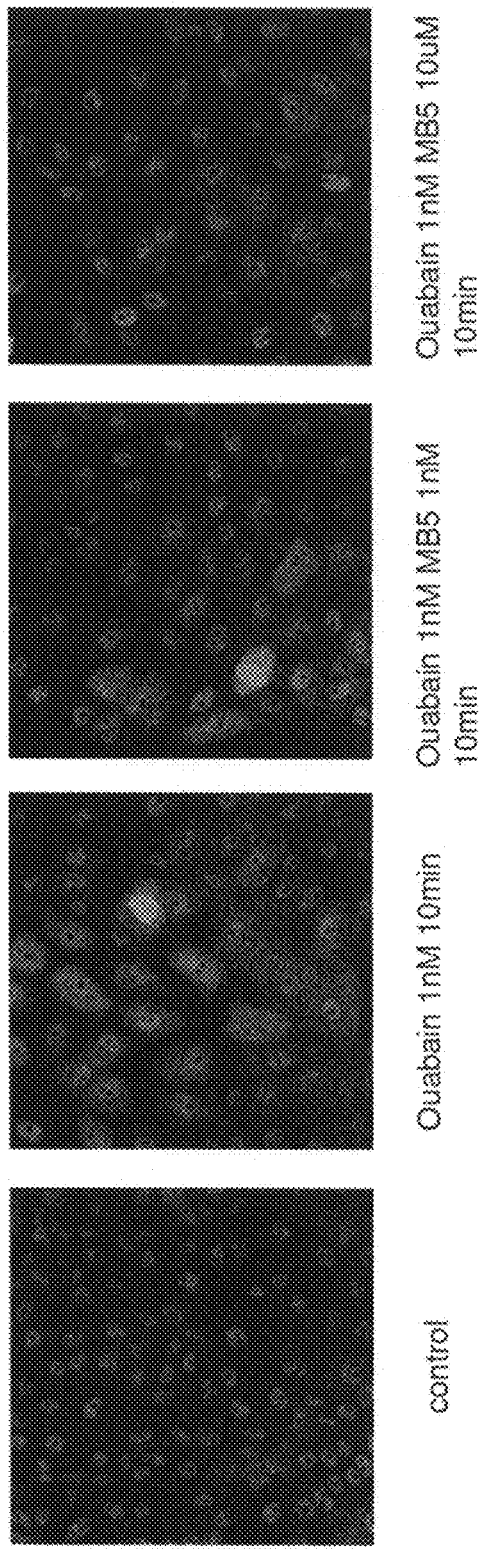
FIG. 9B: Effects of MB5 on ouabain-induced activation of ERKs. LLC-PK1 cells were pretreated with different concentrations of MB5 (1 nM, 10 µM) for 15 min, exposed to 1 nM ouabain for 10 min, and assayed for active ERKs as in FIG. 9A. A representative set of images is shown.
Figure 9C:
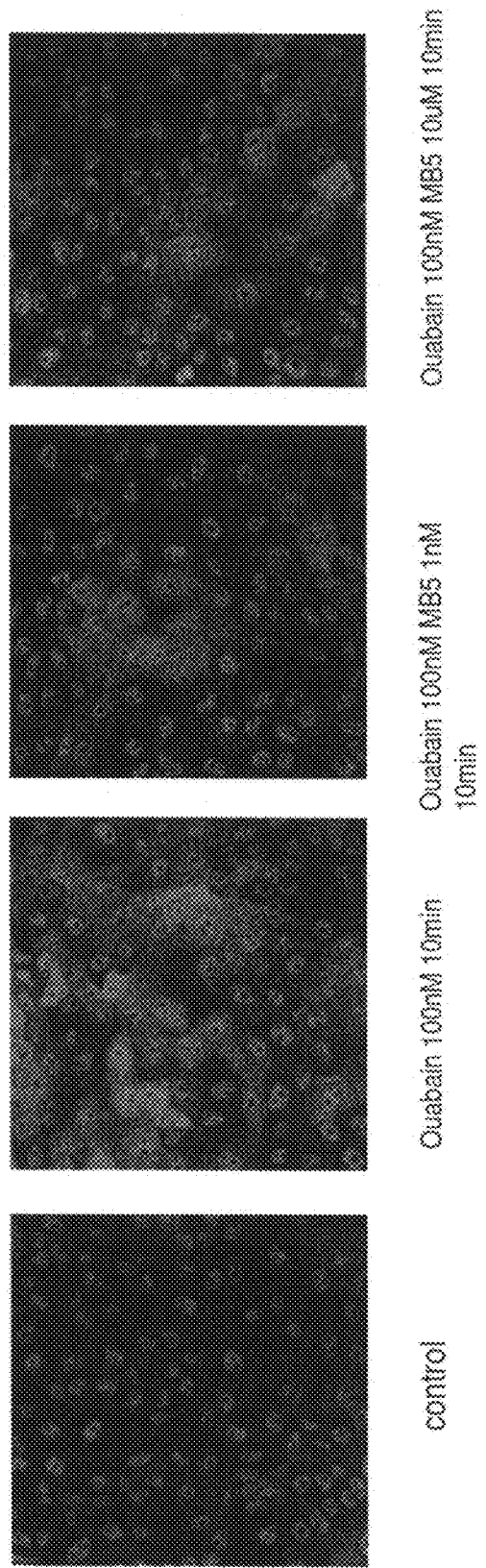
FIG. 9C: Effects of MB5 on ouabain-induced activation of ERKs. LLC-PK1 cells were pretreated with different concentrations of MB5 (1 nM, 10 µM) for 15 min, exposed to 100 nM ouabain for 10 min, and assayed for active ERKs as in FIG. 9A. A representative set of images is shown.
Figure 9D:
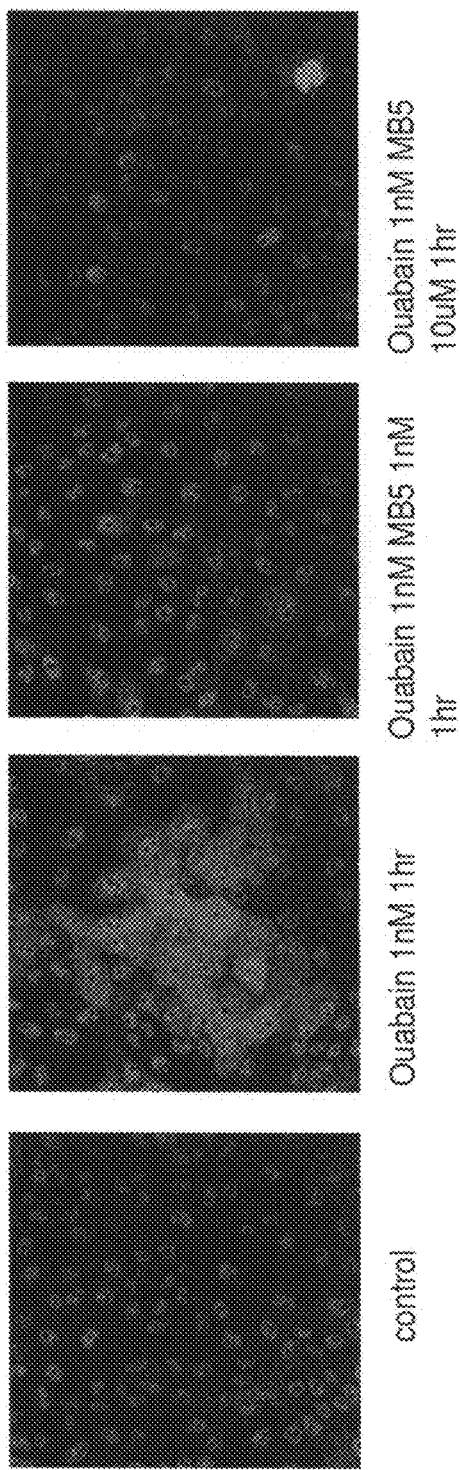
FIG. 9D: Effects of MB5 on ouabain-induced activation of ERKs. LLC-PK1 cells were pretreated with different concentrations of MB5 (1 nM, 10 µM) for 15 min, exposed to 1 nM ouabain for 1 hour, and assayed for active ERKs as in FIG. 9A. A representative set of images is shown.
Figure 9E:
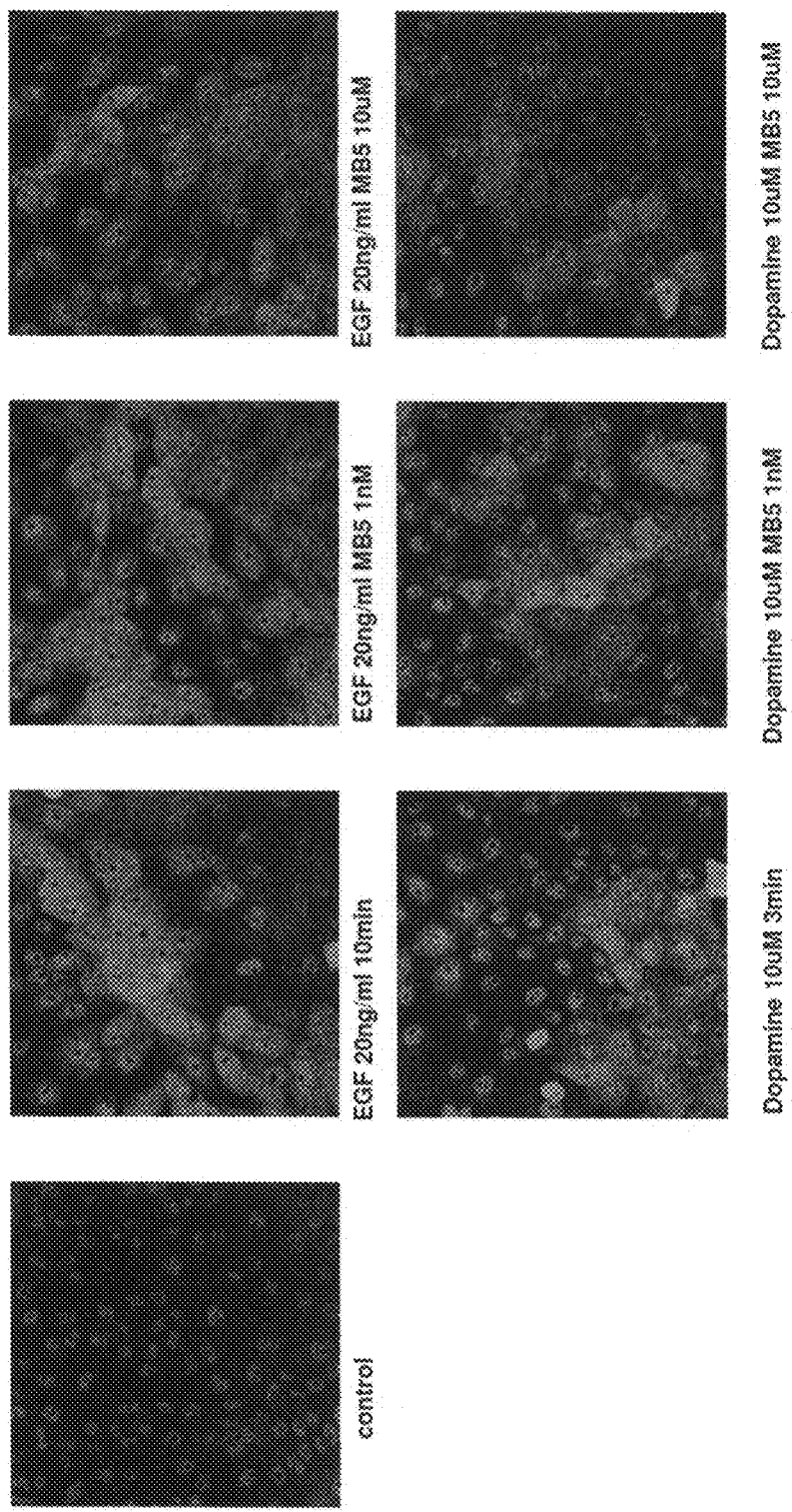
FIG. 9E: Effects of MB5 on stimuli-induced activation of ERKs. LLC-PK1 cells were pretreated with different concentrations of MB5 (1 nM, 10 µM) for 15 min, exposed to epidermal growth factor (EGF) or Dopamine stimuli for either 10 or 3 min, and assayed for active ERKs as in FIG. 9A. A representative set of images is shown.

In contrast, when the same experiments were conducted in the presence of either EGF or dopamine, MB5 failed to affect ERK activation induced by these two stimuli (FIG. 9E).

Taken together, these data show that MB5 can function as a specific ouabain antagonist to against the activation of protein kinase cascades.

Discussion of Example II

The receptor Na/K-ATPase/Src complex can be activated when the Na/K-ATPase is stabilized in the E2 conformation, whereas the E1 Na/K-ATPase keeps Src in an inactive state.

Described herein is an effective high throughput screen assay for chemicals that can regulate both pumping and signaling functions of Na/K-ATPase.

The high throughput assay (as described in EXAMPLE I) is useful to identify chemicals/compositions that affect the E1/E2 conformational transition, as reflected by the inhibition of Na/K-ATPase. The identified chemicals/compositions can then be tested as either agonists or antagonists of Na/K-ATPase/Src receptor complex as follows: As agonists, such chemicals/compositions would function as ouabain and their inhibitory effects on the Na/K-ATPase could be antagonized by increasing K$^+$ concentration. On the other hand, as antagonists they would act as MB5, preventing ouabain binding to the Na/K-ATPase. Moreover, their inhibitory effect on Na/K-ATPase could be reduced by increasing Na$^+$ concentration.

Also described herein is the identification of a class of novel and potent ouabain antagonists that prevent ouabain from activating the Na/K-ATPase/Src receptor complex. Subsequently, the ouabain antagonists also abolished ouabain-induced activation of ERKs.

These results are significant for at least the following considerations: 1) Na/K-ATPase complexes and/or Na/K-ATPase/Src complexes are useful for screening new agonists and antagonists; 2) Xanthone derivatives, as described herein, are useful as medications to antagonize endogenous CTS elevation-induced pathological changes that include, for example, cardiovascular and renal remodeling as well as cardiac and renal fibrosis; 3) Xanthone derivatives, as described herein, are useful as medications to treat congestive heart failure because they can not only improve contractile function but also prevent structural remodeling in the myocardium; 4) Xanthone derivatives, as described herein, are useful as medications to treat prostate and other cancers because the Na/K-ATPase signaling is important for the growth of these cancer cells; and, 5) Xanthone derivatives are useful for the new generation of receptor Na/K-ATPase antagonists that will be more potent, less toxic and have better pharmacokinetic properties than currently available compositions.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof. Therefore, it is intended that the invention not be limited to the particular embodiment disclosed herein contemplated for carrying out this invention, but that the invention will include all embodiments falling within the scope of the claims.

What is claimed is:

1. A method for inhibiting cancer cell proliferation comprising:
   administering to a subject in need thereof an effective amount of at least one Na/K-ATPase ligand selected from the group consisting of: MB5 (3,4,5-trihydroxyxanthone) and MB7 (3,4,5,6-tetrahydroxyxanthone); and
   inhibiting the ATPase activity without stimulating the receptor function of Na/K-ATPase in the subject in need of inhibition of cancer cell proliferation.

2. The method of claim 1, wherein the Na/K-ATPase ligand is MB5 (3,4,5-trihydroxyxanthone).

3. The method of claim 1, wherein the Na/K-ATPase ligand is MB7 (3,4,5,6-tetrahydroxyxanthone).

4. The method of claim 2, wherein the Na/K-ATPase ligand is present at 1.0 nM.

* * * * *